United States Patent [19]

Gavin et al.

[11] Patent Number: 5,731,212

[45] Date of Patent: *Mar. 24, 1998

[54] TEST APPARATUS AND METHOD FOR TESTING CUVETTE ACCOMMODATED SAMPLES

[75] Inventors: Michael Gavin, Warren, N.J.; James A. Mawhirt, Brooklyn, N.Y.; Donald W. Allen, Point Pleasant, N.J.

[73] Assignee: International Technidyne Corporation, Edison, N.J.

[*] Notice: The term of this patent shall not extend beyond the expiration date of Pat. No. 5,504,011.

[21] Appl. No.: 359,923

[22] Filed: Dec. 20, 1994

[51] Int. Cl.$^6$ .................. G01N 33/553; G01N 33/558

[52] U.S. Cl. .................. 436/526; 356/244; 356/246; 422/55; 422/57; 422/58; 422/68.1; 422/73; 422/81; 422/82.01; 422/82.02; 435/287.1; 435/287.2; 435/287.9; 435/288.2; 435/288.4; 435/288.5; 435/288.7; 435/810; 436/514; 436/518; 436/524; 436/525; 436/536; 436/805; 436/806; 436/809

[58] Field of Search .................. 356/244, 246; 422/55, 57, 58, 68.1, 73, 81, 82.01, 82.02, 82.13; 435/287.1, 287.2, 287.9, 288.2, 288.4, 288.5, 288.7, 810; 436/514, 518, 524, 525, 526, 805, 806, 807, 809, 536

[56] References Cited

U.S. PATENT DOCUMENTS

| | | |
|---|---|---|
| 2,616,796 | 11/1952 | Schilling et al. |
| 3,302,452 | 2/1967 | Leslie. |
| 3,486,859 | 12/1969 | Grenier et al. |
| 3,635,678 | 1/1972 | Seitz et al. |
| 3,695,482 | 10/1972 | Smith. |
| 3,699,437 | 10/1972 | Ur. |
| 3,836,333 | 9/1974 | Mintz. |
| 3,918,908 | 11/1975 | Moyer et al. |
| 4,000,972 | 1/1977 | Braun et al. |
| 4,034,601 | 7/1977 | Geiger. |
| 4,074,971 | 2/1978 | Braun et al. |
| 4,105,411 | 8/1978 | Biver. |
| 4,125,327 | 11/1978 | Margolis. |
| 4,135,819 | 1/1979 | Schmid-Schonbein. |
| 4,443,408 | 4/1984 | Mintz. |
| 4,454,752 | 6/1984 | Scordato. |
| 4,497,774 | 2/1985 | Scordato. |
| 4,534,939 | 8/1985 | Smith et al. |
| 4,599,219 | 7/1986 | Cooper et al. |
| 4,640,896 | 2/1987 | Farrell et al. |
| 4,659,550 | 4/1987 | Schildknecht. |
| 4,663,127 | 5/1987 | Jackson et al. |
| 4,671,939 | 6/1987 | Mintz. |
| 4,752,449 | 6/1988 | Jackson et al. |

(List continued on next page.)

FOREIGN PATENT DOCUMENTS

| | | |
|---|---|---|
| 3540661A1 | 11/1985 | Germany. |
| WO9101383 | 2/1991 | WIPO. |
| WO9116453 | 10/1991 | WIPO. |

*Primary Examiner*—Christopher L. Chin
*Attorney, Agent, or Firm*—Plevy & Associates

[57] ABSTRACT

A cuvette based testing device for use in testing or otherwise analyzing a fluid sample. A cuvette is provided that defines at least one conduit, wherein the fluid sample is introduced into the various conduits. Reagents are disposed within the conduits that are intended to be mixed with the fluid sample. The fluid sample is drawn into the conduits by the force of a pneumatic pump. As the fluid sample contacts the various reagents, the reagents mix with the sample. Mixing is further conducted by moving the fluid sample back and forth across an obstruction in the conduit. The obstruction causes turbulent flow in the fluid sample, thereby mixing the sample with any reagent also present. The conduit is preferably transparent. The fluid sample is brought to a point in the cuvette where it is disposed below a detector. The detector is used to measure a characteristic of the fluid sample such as optical density, nephelometry, fluorescence, chemical luminescence, photoemittions or the like. By knowing the reagents mixed with the sample and measuring one or more characteristics of the fluid sample, the sample can be accurately analyzed for many differing tests.

35 Claims, 10 Drawing Sheets

U.S. PATENT DOCUMENTS

| | | |
|---|---|---|
| 4,756,884 | 7/1988 | Hillman et al. . |
| 4,780,418 | 10/1988 | Kratzer . |
| 4,782,026 | 11/1988 | Baugh et al. . |
| 4,865,984 | 9/1989 | Nemerson et al. . |
| 4,871,677 | 10/1989 | Baugh et al. . |
| 4,946,775 | 8/1990 | Yin . |
| 5,147,607 | 9/1992 | Mochida . |
| 5,167,145 | 12/1992 | Butler et al. . |
| 5,223,219 | 6/1993 | Subramanian et al. . |
| 5,302,348 | 4/1994 | Cusack et al. . |
| 5,304,487 | 4/1994 | Wilding et al. ............... 435/7.2 |
| 5,366,869 | 11/1994 | Goldstein . |
| 5,486,335 | 1/1996 | Wilding et al. ............... 422/58 |
| 5,503,985 | 4/1996 | Cathey et al. ............... 475/7.9 |
| 5,504,011 | 4/1996 | Gavin et al. ............... 422/73 |

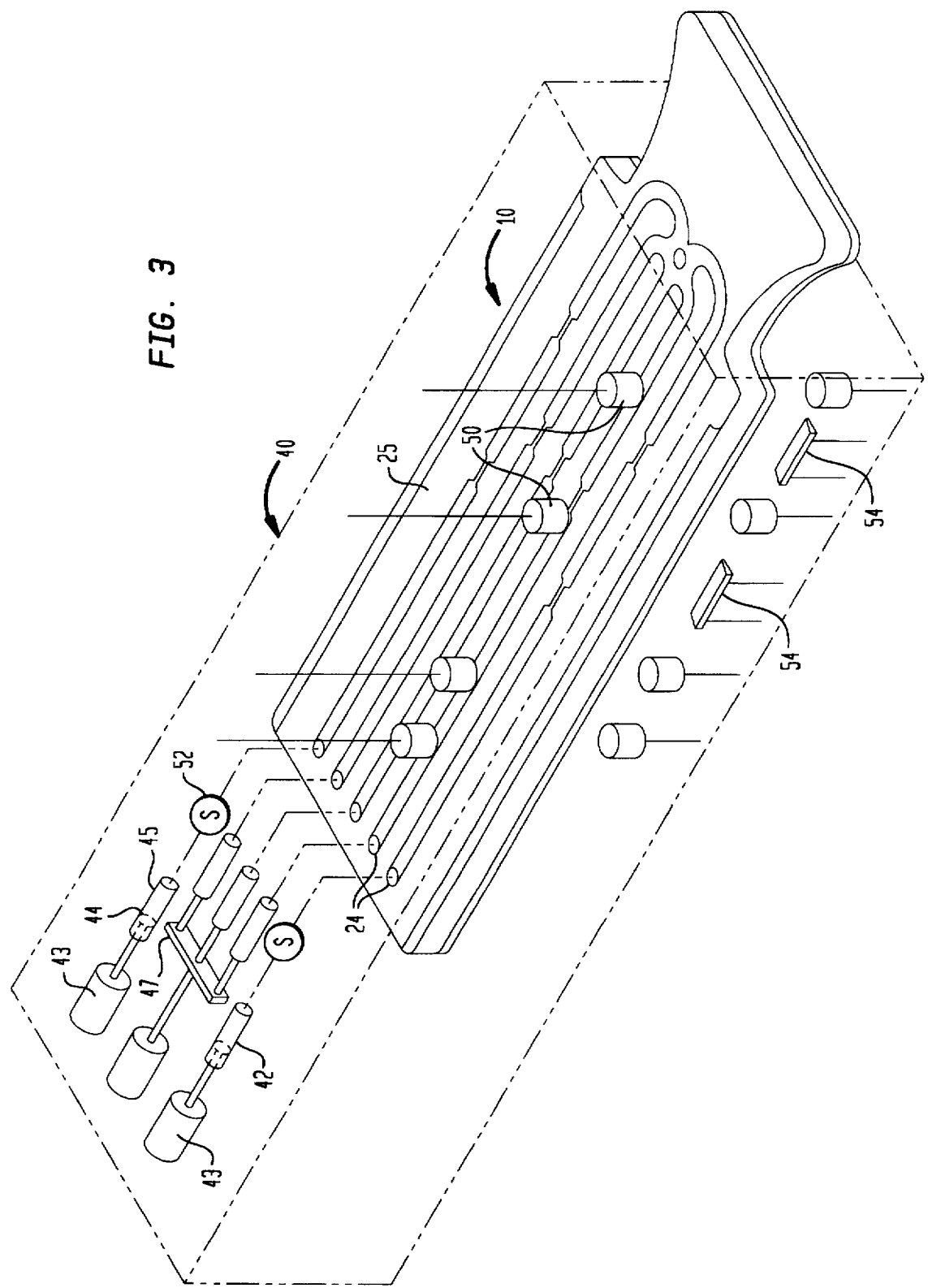

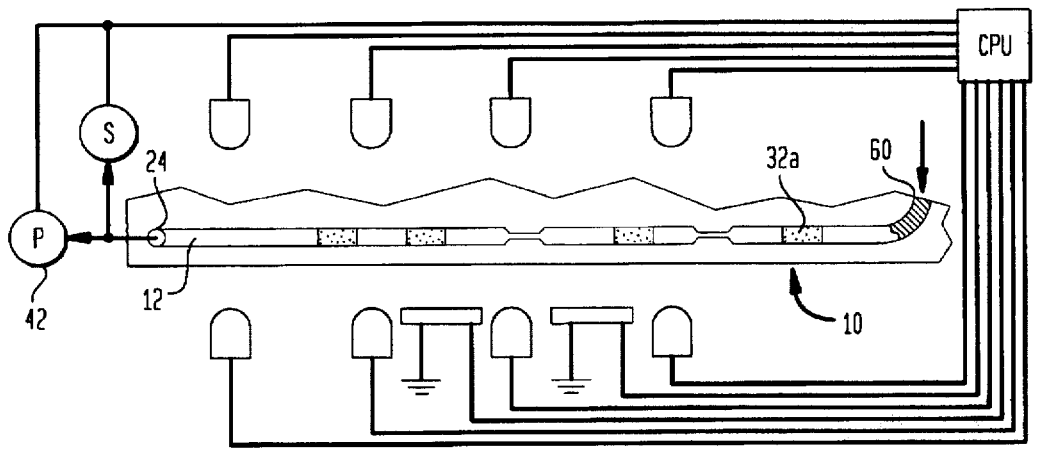
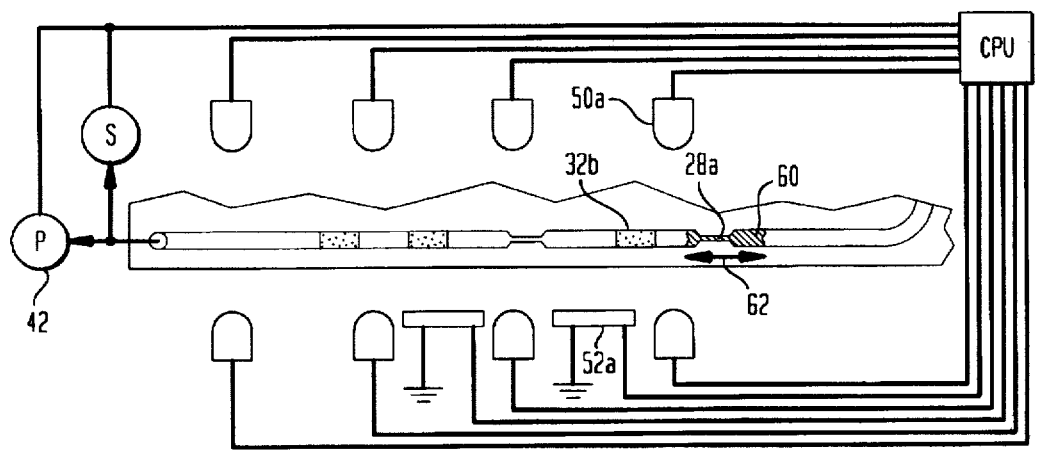
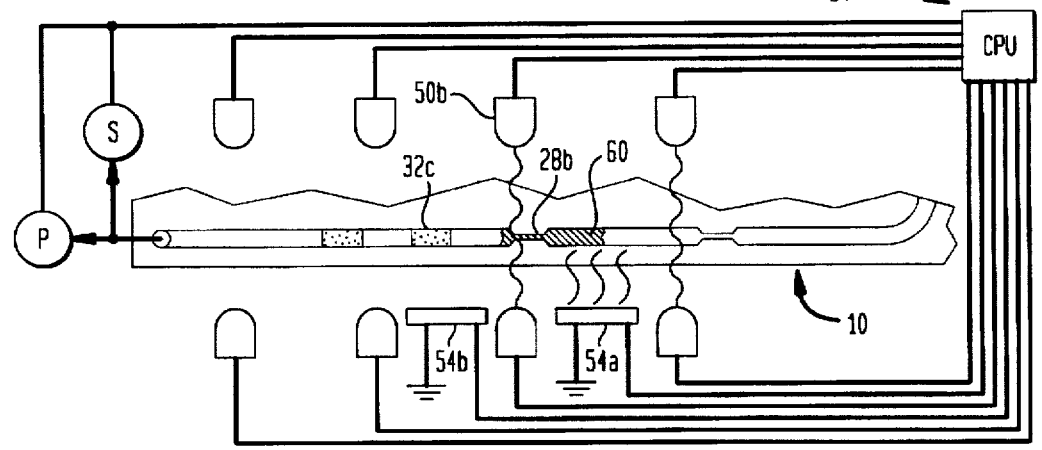

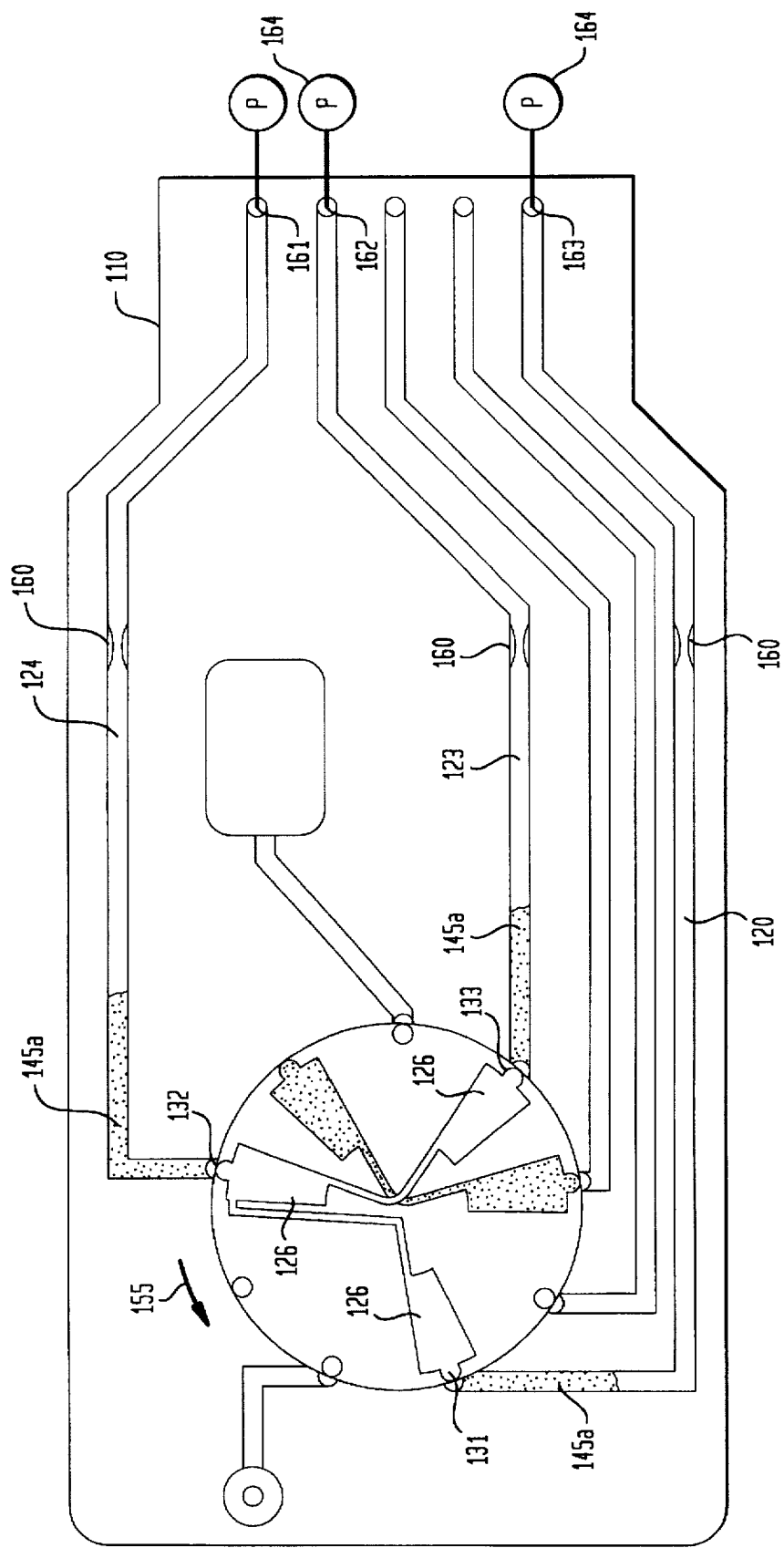

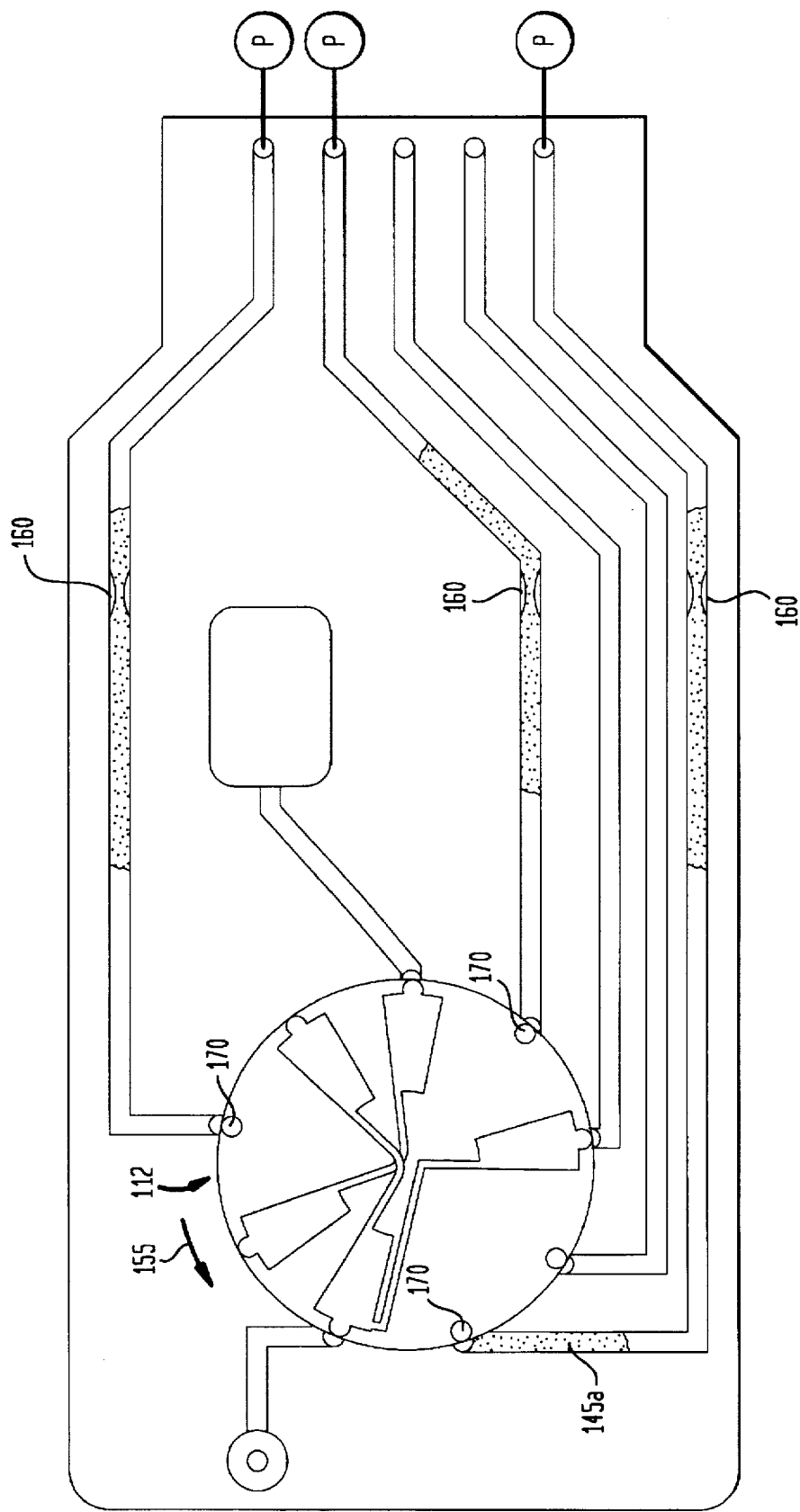

TEST APPARATUS AND METHOD FOR TESTING CUVETTE ACCOMMODATED SAMPLES

RELATED APPLICATIONS

The subject matter of this application is related to the subject matter of U.S. patent application Ser. No. 08/327, 320, filed Oct. 21, 1994, entitled PORTABLE TEST APPARATUS AND ASSOCIATED METHOD OF PERFORMING A BLOOD COAGULATION TEST, now U.S. Pat. No. 5,504,011, which is assigned to International Technidyne Corporation, the assignee herein.

U.S. Pat. No. 5,302,348 to Cusack et al, entitled BLOOD COAGULATION TIME TEST APPARATUS AND METHOD, is incorporated into this application by reference.

BACKGROUND OF THE INVENTION

1. Field of the Invention

The present invention relates to testing devices for testing liquid samples, wherein the liquid samples are tested within disposable cuvettes. More particularly, the present invention relates to the structure of the cuvette, the testing device and the method of how the testing device works in unison with the structure of the cuvette to manipulate the liquid sample in the cuvette as a test is being performed.

2. Prior Art Statement

There are a multitude of liquid compounds used throughout chemistry, medicine and engineering that have variable characteristics that can only be ascertained through sample testing. For instance, in medicine, if a practitioner wants to know the coagulation characteristics of a patient's blood that information can only be accurately ascertained by testing a sample of that patient's blood and physically measuring its coagulation characteristics.

In the prior art, many devices have been developed to test specific characteristics of various liquid compounds. In many cases, a sample of the liquid compound is taken and inserted into the testing device. The sample contaminates the various components of the testing device, thereby requiring the testing device to be either disposed of, cleaned or otherwise purged of the contaminants before a test of another sample can be performed. Obviously, the time and labor involved in purging a testing machine between tests are undesirable by-products of sample testing.

In an attempt to greatly reduce the time and labor involved in purging testing machines in between tests, testing machines have been developed that test liquid compounds contained within self-contained disposable cassettes or cuvettes. In such testing systems, only the disposable cassette or cuvette becomes contaminated during the test. To prepare the testing machine for a new test, the old cassette or cuvette is removed and replaced by a new cassette or cuvette containing the new test sample. Such prior art test systems are exemplified by U.S. Pat. No. 5,039,617 to McDonald et al, entitled, CAPILLARY FLOW DEVICE AND METHOD FOR MEASURING ACTIVATED PARTIAL THROMBOPLASTIN TIME.

A problem with many prior art testing systems that use cuvettes to retain liquid test samples is that the test samples are often required to flow within the cuvettes propelled solely by capillary action. Capillary action provides only a one way flow that prevents the sample from being moved reciprocally within the cuvette. Capillary action is constant and prevents the sample from being temporarily paused in one position for testing before it can be advanced to a second location. Furthermore, the manufacturing of a cuvette that uses capillary action is very difficult. If a capillary conduit in a cuvette is made too large, capillary flow will not occur. Similarly, if a capillary conduit in a cuvette is made too small, the surface tension of the test fluid may prevent it from flowing evenly through the conduits. As such, cuvettes that rely solely upon capillary action to move the test sample must have unnecessarily high quality controls to ensure that the various capillary conduits remain in a predetermined range. The critical nature of the manufacturing process adds significantly to the cost of such capillary cuvettes.

Because of the limitations of capillary cuvettes, many liquid compound tests can not be easily adapted to the use of cuvette technologies. For example, many tests require that the liquid sample be mixed with various other compounds during the course of its testing. Still other tests require that the compound be given time to react with a reagent before it is advanced further within a cuvette for testing.

Another disadvantage of testing devices that utilize cuvettes is that it is very difficult to mix reagents with the test compound within the confines of the narrow conduits defined by the cuvette. In the conduits of a cuvette, a desired reagent can only be mixed with a liquid test sample by bringing the test sample in contact with the reagent within one of the narrow cuvette conduits. The reagent itself can not be a liquid, else it would migrate in the cuvette conduits by the same forces used to move the test sample within the cuvette conduits. The reagent in the cuvette conduits also can not be a solid that significantly blocks the conduit opening, else the reagent would cause a pneumatic obstruction that would prevent the test sample from reaching the reagent via capillary action or pneumatic pumping. To solve this problem, many prior art cuvettes are manufactured with enlarged reaction chambers. See for example U.S. Pat. No. 5,147,606 to Charlton et al, entitled SELF-METERING FLUID ANALYSIS DEVICE. This provides the space needed for the test sample to properly mix with the reagent.

The use of enlarged reaction chambers within a cuvette consumes a large amount of the space available on a cuvette, thereby making it difficult to place multiple testing conduits in the same cuvette. The presence of enlarged reaction chambers enable test fluid to come into contact with reagents within the cuvette, however, no mechanism is provided for actively mixing the test fluid with the reagent. As a result, even though the test fluid meets a given reagent, the reagent is not thoroughly mixed with the test fluid and the concentration of the reagent varies greatly from one part of the test fluid to another. The variation of the reagent concentrations can cause large discrepancies in the results of tests on the same fluid, thereby detracting from the reliability and consistency of the test being performed.

It is therefore an object of the present invention to provide a disposable testing cuvette that does not rely upon capillary action to move testing fluid between points for testing.

It is a further object of the present invention to provide a disposable testing cuvette and test system embodying a means for actively mixing compounds within the cuvette.

It is yet another object of the present invention to provide a disposable testing cuvette that is inexpensive to manufacture and contains regents capable of mixing with the test fluid within the cuvette without the need for enlarged reaction chambers.

SUMMARY OF THE INVENTION

The present invention is a cuvette based testing device for use in testing or otherwise analyzing a fluid sample. A cuvette is provided that defines at least one conduit, wherein the fluid sample is introduced into the various conduits. Reagents are disposed within the conduits that are intended to be mixed with the fluid sample. The fluid sample is drawn into the conduits by the force of a pneumatic pump. As the fluid sample contacts the various reagents, the reagents mix with the sample. Mixing is further conducted by moving the fluid sample back and forth across an obstruction in the conduit. The obstruction causes turbulent flow in the fluid sample, thereby mixing the sample with any reagent also present. The conduit is preferably transparent. The fluid sample is brought to a point in the cuvette where it is disposed below a detector. The detector is used to measure a characteristic of the fluid sample such as optical density, nephelometry, fluorescence, chemical luminescence, photo-emissions or the like. By knowing the reagents mixed with the sample and measuring one or more characteristics of the fluid sample, the sample can be accurately analyzed for many differing tests.

The test cuvettes each preferably contain multiple conduits that all draw the fluid sample from a common source. As a result, different reagent combinations can be disposed in the different conduits. This enables multiple tests of the same fluid sample to be performed simultaneously within the same cuvette.

BRIEF DESCRIPTION OF THE DRAWINGS

For a better understanding of the present invention, reference is made to the following description of exemplary embodiments thereof, considered in conjunction with the accompanying drawings, in which:

FIG. 3 is a perspective view of the cuvette of FIG. 1, shown in conjunction with a schematic representation of one preferred embodiment of a test apparatus;

FIGS. 4a–4f show a fragmented view of one portion of the cuvette of FIG. 1, shown in conjunction with a schematic representation of a test apparatus and containing a fluid sample to show the operation of the test apparatus;

FIGS. 7a–7d are a cross-sectional view of the cuvette shown in FIG. 6, viewed along sectional line 7—7;

DETAILED DESCRIPTION OF THE PRESENT INVENTION

Although the present invention can be used in many different applications where the variable characteristics inherent in a liquid sample need to be tested, such as the effects of various variables in a chemical polymerization reaction, the present invention is especially suitable for use in testing bodily fluids such as whole blood, plasma, serum, urine, sputum, bile and the like. Accordingly, the present invention will be described in connection with a blood testing scenario in order to provide on exemplary embodiment of the function of the present invention.

Figure 1:
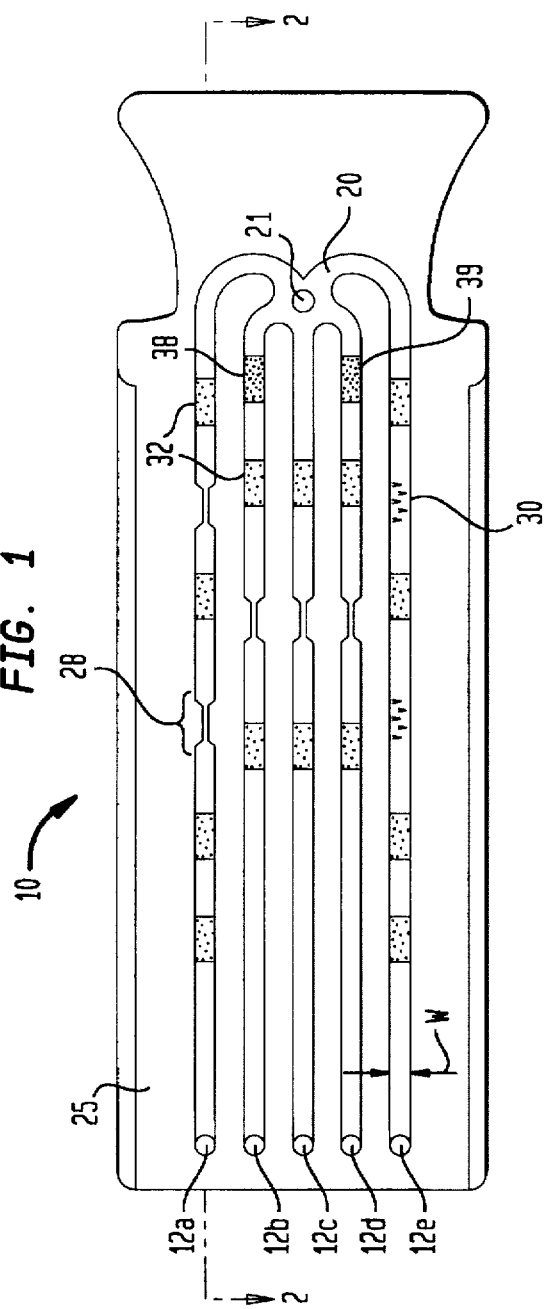
FIG. 1 is a top view of one preferred embodiment of a cuvette for use in conjunction with the present invention test apparatus.
Figure 2:
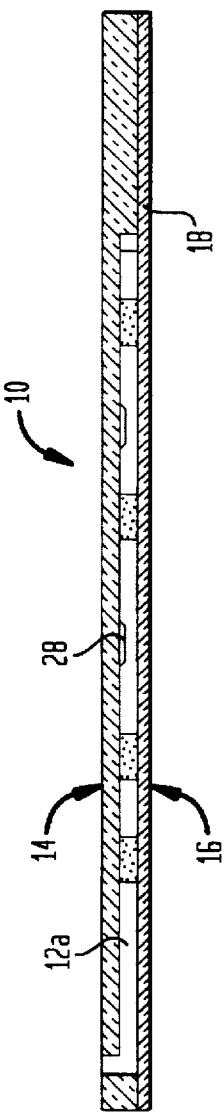
FIG. 2 is a cross-sectional view of the embodiment of FIG. 1 viewed along sectional line 2—2.

Referring to FIG. 1, in configuration with FIG. 2, a cuvette 10 is shown. A plurality of conduits 12a, 12b, 12c, 12d, 12e (FIG. 1) are defined within the cuvette 10. Although five conduits are shown, it will be understood that the cuvette 10 may define a single conduit or any plurality of conduits as desired.

The cuvette 10 is preferably made of a transparent material for a purpose which will later become apparent. In FIG. 2 it can be seen that the cuvette 12 is made of two pieces of transparent material. The upper portion 14 of the cuvette 10 is a solid piece into which the various conduits are formed. The conduits can be molded into the bottom surface 18 of the upper portion 14. However, the conduits may be machined, etched or otherwise formed depending upon the material selected for the upper portion 14. A solid lower portion 16 is coupled to the bottom surface 18 of the upper portion 14. The lower portion 16 is preferably bonded to the bottom surface 18 of the upper portion 14, thereby cooperating with the upper portion 14 in defining each of the conduits 12a, 12b, 12c, 12d, 12e (FIG. 1). The lower portion 16 of the cuvette 10 is preferably a thin, flexible laminate that is smooth on both its surfaces, thereby not requiring etching, machining or other precision work. By molding grooves in the upper portion 14 and bonding a laminate over the grooves, the various conduits 12a, 12b, 12c, 12d, 12e are constructed in a highly accurate and cost effective manner.

In FIG. 2 only the first conduit 12a is shown. Although each of the conduits could be sized differently, each conduit in the cuvette 10 should have a height H and a width W (FIG. 1) large enough to prevent a significant amount of capillary flow within the conduits. Since capillary flow is a function of the viscosity of the fluid flowing, it will be understood that the height H and width W of each of the conduits is dependant upon what type of fluid eventually will be tested within the cuvette 10.

Returning to FIG. 1, it can be seen that each of the multiple conduits 12a, 12b, 12c, 12d, 12e intersects a common supply area 20. An aperture 21 is disposed in the common supply area 20 thereby providing an entrance through which test fluid can be introduced into the cuvette 10. The opposite end of each of the conduits 12a, 12b, 12c, 12d and 12e, terminates at a pumping port 24 (shown in FIG. 3) that extends up through the top surface 25 of the cuvette 10. At least one mixing obstruction can be disposed at any desired point within any or all of the conduits 12a, 12b, 12c, 12d, 12e. In the shown embodiment, two different types of mixing obstructions are illustrated. The first type is a restricted region 28 positioned in at least one place along the length of a conduit. As will be later explained, the restricted region 28 causes turbulence that mixes fluid flowing past it within the conduit. Looking briefly at FIG. 2, it can be seen that the restricted region 28 is formed solely in the upper portion 14 of the cuvette 10. This way the restricted region 28 can be molded or otherwise formed as part of the cuvette's upper portion 14 and need not be dependent upon the shape of the cuvette's lower portion 16. As a result, the lower portion 16 can remain a flat, low cost laminate. This one sided restriction makes the cuvette 10 much simpler to manufacture and assemble compared to a two piece cuvette where the two pieces would have to be aligned to properly form the restriction. The preferred shape of the restriction region is described and illustrated in U.S. Pat. No. 5,302,348 to Cusack et al, entitled BLOOD COAGULATION TIME TEST APPARATUS AND METHOD, and assigned to the assignee herein, the Cusack patent being incorporated herein by reference.

The first four conduits 12a, 12b, 12c and 12d all contain at least one restricted region 28. The fifth conduit 12e shows an alternate mixing obstruction. These alternate mixing obstructions are small protrusions 30 that extend into the conduit 12e. The small protrusions 30 create turbulence in a test fluid as the test fluid flows over the protrusions 30 much in the same manner that stones in a stream cause turbulence in the flow of water. As will be later explained, the turbulent flow created by the small protrusions 30 acts to mix the test fluid within the confines of the conduit 12e.

Many test fluids are tested by combining the test fluid with reagent compounds to see if certain characteristics of the test fluid change. Such changes may include a change in viscosity, fluorescence, chemical luminescence, impedance, optical density, nephelometry or any other measurable characteristic. By determining the change that occurred in the test fluid, information is yielded regarding the characteristics of the original test fluid. An obvious example would be a home pregnancy test. In such a test, urine is mixed with compounds that change color if the urine contains certain target hormones associated with pregnancy. By viewing the change in color, a person can ascertain that the test fluid (i.e. urine) contained those target hormones.

In the present invention, the reagent compounds 32 intended to be mixed with the test fluid are contained with the various conduits 12a, 12b, 12c, 12d, 12e. In the preferred embodiment, the reagent compounds 32 are dried, wherein a test fluid rehydrates the reagent compounds 32 when the test fluid flows across the reagent compounds 32. The reagent compounds 32 do not substantially obstruct the conduits 12a, 12b, 12c, 12d, 12e, but rather are a thin deposit of materials dried to the walls of the conduits. The reagent compounds 32 are deposited into the various conduits 12a, 12b, 12c, 12d, 12e as the cuvette 10 is manufactured. The reagent compounds 32 are deposited as liquid slugs in each of the conduits before the lower portion 16 (FIG. 2) of the cuvette 10 is joined to bottom surface 18 of the cuvette's upper portion 14. Once isolated within the cuvette 10, the reagent compounds 32 are preferably dried by a lyophilization process or other liquid extraction technique. In the shown embodiment, the first conduit 12a and the last conduit 12e each contain four separate reagent compounds. The middle three conduits 12b, 12c, 12d each contain two separate reagent compounds. From such a configuration, it should be understood that any number of reagent compounds 32 can be placed in each of the conduits 12a, 12b, 12c, 12d, 12e and the reagent compounds can vary in number, composition and position from one conduit to another depending upon the fluid being tested and the test being performed.

Since each of the multiple conduits 12a, 12b, 12c, 12d, 12e can contain its own unique configuration of reagent compounds 32 and mixing obstructions, and each of the conduits draws fluid from a common supply, it will be understood that each of the multiple conduits can be used to perform a different test on the same sample or duplicate testing can be performed to ensure the accuracy of the test results. Selective filtering membranes 38, 39 can also be disposed within any plurality or a single one of the conduits. The filtering membranes 38, 39 can be used to separate a test fluid into different components or filter out a target ingredient from the test fluid. For example, suppose the cuvette 10 of FIG. 1 was being used to test whole blood. The filtering membranes 38 in the second conduit 12b could filter the blood so that only the serum components of the blood were able to pass into the conduit 12b. The filtering membrane 39 in the forth conduit 12d could filter the blood so that only the plasma components of the blood would pass into the conduit 12d. As such, from a single sample of whole blood, the serum, plasma and whole blood can be simultaneously tested in the same cuvette. Filtering membranes capable of separating blood into its plasma and/or serum components are known in the art of hematology and need not be described herein in detail.

Referring to FIG. 3, it can be seen that when a cuvette 10 is placed within a test machine 40, pneumatic pumps 42 couple to the pumping ports 24 on the top surface 25 of the cuvette 10. As a result, the space within each of the conduits 12a, 12b, 12c, 12d, 12e is pneumatically coupled to a pump capable of either increasing or decreasing the air pressure within the confines of those conduits. In the shown embodiment, the pneumatic pumps 42 are positive displacement pumps that work by the use of a stepper motor 43 that drives a piston 44 back and forth within a pumping chamber 45. By advancing the piston 44 within the pumping chamber 45, air pressure within the conduits can be raised above ambient pressure. Adversely, by retracting the piston 44 within the pumping chamber 45, air pressure within the conduits can be reduced below ambient pressure. In the shown embodiment, there are three pneumatic pumps. Two of the pumps individually engage the first conduit 12a and the last conduit 12e, respectfully. As a result, a test fluid present in either of these conduits can be individually controlled. The middle three conduits 12b, 12c, 12d each share a ganged drive 47 displaced by a single stepper motor. As such, the pneumatic pressure changes in the three center conduits at the same rate, thereby allowing three identical testing schemes to be conducted at the same time. It will be understood that the use of three stepper motors as described is merely an exemplary embodiment. Depending upon the number of conduits in the cuvette and the tests to be performed, each of the conduits may have its own dedicated pump or all the conduits may share the same ganged drive.

Pressure sensors 52 may optionally be coupled to each of the pneumatic couplings that connect the various pneumatic pumps to the conduits 12a, 12b, 12c, 12d, 12e within the cuvette. As will later be explained, the pressure sensors 52 can measure the pressure within each of conduits, thereby providing a value from which the viscosity of a test fluid can be ascertained, since it is known that the viscosity is proportional to the displacement of the sample in the cuvette in response to a given pressure.

When the cuvette 10 is placed within the test machine 40, the various conduits 12a, 12b, 12c, 12d, 12e each align either above or below a series of detectors 50. The detectors 50 are any detectors capable of measuring a physical characteristic of any test fluid present within one of the conduits. For instance, the detectors could be photo multiplier tubes to detect fluorescence and chemical luminescence, photo detectors to detect physical presence and nephelometry, infrared detectors for detecting optical density or any combination thereof. The detectors 50 align over various detection zones in each conduit where a test fluid will stand ready to be tested.

Small heating elements 54 may be disposed below different areas of each of the conduits 12a, 12b, 12c, 12d, 12e. The heating elements 54 are used to heat different areas of a conduit at different times in order to facilitate a desired reaction of a test fluid contained within the conduit.

Although multiple heating elements 54 provide more complex control of the temperature of the test fluid in a conduit, it will be understood that certain tests do not require different temperature zones. Accordingly, a single heating element could be used to heat the entire cuvette 10 to a predetermined temperature prior to testing.

Referring to FIG. 4a, a segment of the cuvette 10 is shown containing just one of the conduits 12 contained within the cuvette 10. A fluid test sample 60 is introduced into the common supply area 20 (FIG. 1) in a conventional manner such as those described in co-pending U.S. patent application Ser. No. 08/327,320, entitled PORTABLE TEST APPARATUS AND ASSOCIATED METHOD OF PERFORMING A BLOOD COAGULATION TEST. The test sample 60 is drawn into the conduit 12 by the pneumatic pump 42 that lowers the air pressure within the conduit 12, via the pumping port 24 at the far end of the cuvette 10. As the test sample 60 is drawn into the conduit 12, it is brought into contact with a dried reagent compound 32a, wherein the test fluid 60 rehydrates the reagent compound 32a. As has been previously explained, the reagent compounds within each conduit can be any substance that alters a chemical and/or physical characteristic of the test sample. For example, if the test sample were blood, the reagent could be a coagulant or an anticoagulant, thereby altering the clotting characteristics of the sample.

In FIG. 4b, it can be seen that the pneumatic pump 42 can be reversed. As a result, the test sample 60 can be reciprocally moved back and forth within the conduit 12, as indicated by arrow 62. To help mix the first reagent compound 32a with the test sample 60, the test sample 60 can be reciprocally moved back and forth through a first restricted region 28a. The restricted region 28a creates turbulence in the flow of the test sample 60 that mixes the test sample with the reagent compound within the confines of the conduit 12. The first set of detectors 50a is present proximate the first reagent compound 32 (FIG. 4a). The first set of detectors 50a may be a photodetector that detects the presences of the test sample 60 and triggers the reversal of the pneumatic pump 42, via the central processing unit (C.P.U) 64. However, the first set of detectors 50a may also be sensors capable of actually measuring a characteristic of the test sample 60. For example, the sensors may detect photoluminescence from the sample or may measure optical density or nephelometry.

After a predetermined mixing period has passed or a given test has been conducted, the test sample 60 may be advanced across a second reagent compound 32b. As with the first reagent compound, the test sample 60 rehydrates the second reagent compound 32b and mixes therewith. A first heating elements 52a may be disposed in the area below the second reagent compound 32b. The heating element 52a may be used to raise the temperature of the conduit 12 in the region of the second reagent compound 32b without significantly effecting the temperature in other regions of the conduit 12.

In FIG. 4c, it is shown that as the test sample 60 rehydrates the second reagent compound 32b (FIG. 4b), it is heated by the heating element 54a. Such a construction is merely exemplary and it will be understood that the heating element 54a need only be present if it is desired to raise the temperature of the test sample 60 to create a certain reaction with the second reagent compound 32b or create some other useful result. A second restricted region 28b is disposed proximate the second reagent compound 32b. The test sample 60 can be reciprocally passed through the second restricted region 28b to mix the test sample 60 with the second reagent compound 32b. A second set of detectors 50b is present proximate the second reagent compound 32b. The second set of detectors 50b may be a photodetector that detects the presence of the test sample 60 and triggers the reversal of the pneumatic pump 42, via the central processing unit 64. However, the detectors 50b may be sensors capable of actually measuring a characteristic of the test sample 60, such as photoluminences, optical density or nephelometry.

After a predetermined mixing period has passed or a given test has been conducted, the test sample 60 may be advanced toward a third reagent compound 32c. The test sample 60 rehydrates the third reagent compound 32c and mixes with the compound. A second heating element 54b may be disposed in the area below the third reagent compound 32b. The heating element may be used to raise the temperature of the conduit 12 in the region of the third reagent compound 32c without significantly effecting the temperature in the other region of the conduit 12.

Figure 4D:
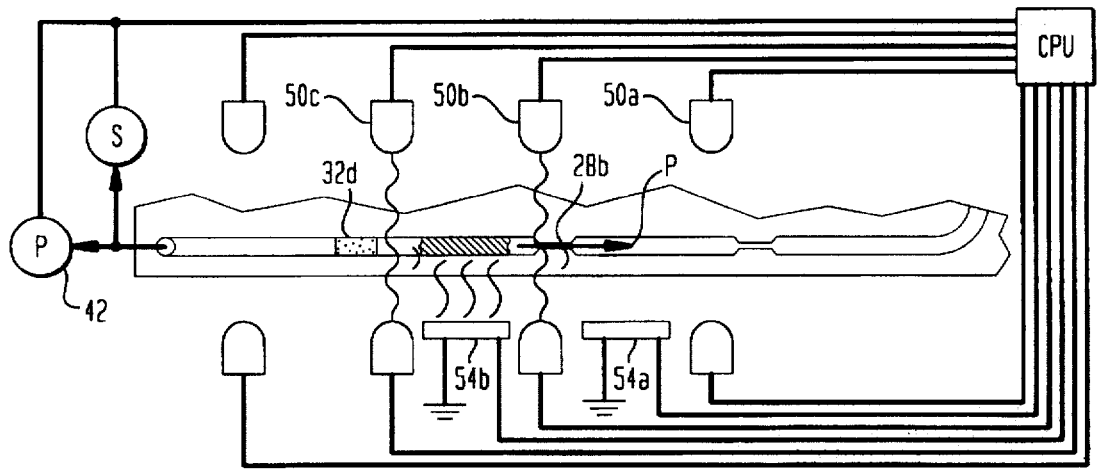

In FIG. 4d, the test sample 60 is shown mixed with the rehydrated third reagent compound 32c (FIG. 4c), as it is being heated by the second heating element 54b. To help facilitate the mixing of the third reagent compound 32c with the test sample 60, the test sample can be repeatedly moved to point P back through the second restricted region 28b. A third set of detectors 50c is present proximate the third reagent compound 32c. The third set of detectors 50c may be a photodetector that detects the presence of the test sample 60 and triggers the reversal of the pneumatic pump 42. Alternatively, the third set of detectors 50c may be sensors capable of actually measuring a characteristic of the test sample 60, such as photoluminences, optical density or nephelometry. Since the test sample can be moved below the third set of detectors 50c, or even the second or first set of detectors 50b, 50c, it will be understood that after the third reagent compound 32c is mixed with the test sample 60, different tests can be conducted on the test sample 60 by the different sets of detectors.

Figure 4E:
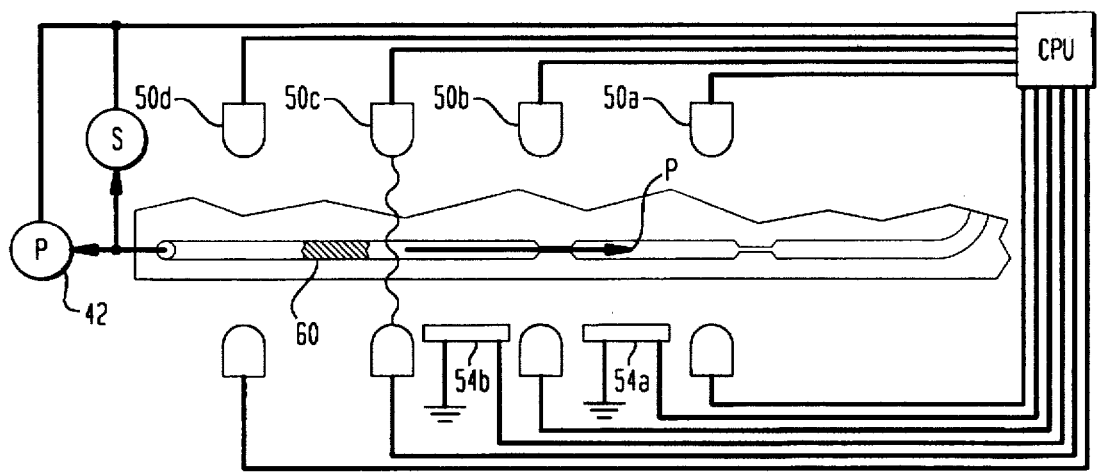

After a predetermined mixing period has passed or a given test has been conducted, the test sample 60 may be advanced toward a fourth reagent compound 32d. The test sample 60 rehydrates the fourth reagent compound 32d and mixes with the compound. In FIG. 4e, the test sample 60 is shown mixed with the rehydrated fourth reagent compound 32e. After the fourth reagent compound 32e is rehydrated, the test sample 60 can be moved to point P back through the second restricted 28b to promote mixing. Also, the test sample 60 can be moved back over one of the heating elements 54a, 54b if it is desired to heat the test sample 60 to a predetermined temperature. The fourth set of detectors 50d may be a photodetector that detects the presence of the test sample 60. Alternatively, the fourth set of detectors 50d may be sensors capable of measuring a characteristic of the test sample 60, such as photoluminence, optical density or nephelometry. Since the test sample can be moved below the fourth set of detectors 50d or any of the other sets of detectors, it will be understood that after the fourth reagent compound 32d is mixed with the test sample 60, different tests can be conducted on the test sample 60 by the different sets of detectors.

Figure 4F:
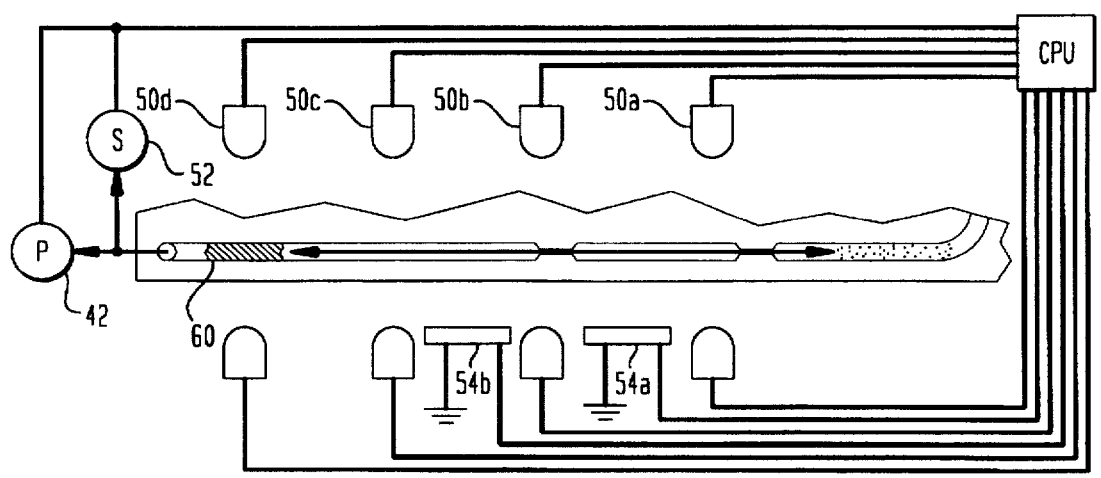

As is shown in FIG. 4f, after the test sample 60 is mixed with the various reagents contained within the conduit 12, the test sample 60 can be moved to any point within the confines of the conduit 12. As a result, any of the different sets of detectors 50a, 50b, 50c, 50d can be used to perform tests with or without the benefits of the heating elements 54a, 54b. Other tests to be performed can be dependent upon the flow characteristics of the test sample 60 in the conduit 12 rather than the test of the optical properties of the test sample. For instance, if the detectors were photo sensors, the time it takes the test sample to move from one point to another can be measured. As a result, the degree of blood coagulation, monomer polymerization, compound curing and other flow rate parameters can be determined. Also by measuring the pressure within the conduit 12a, via a pressure sensor 52, and measuring how fast the test fluid moves in response to a predetermined pressure, the viscosity of the test sample 60 can be determined.

It will be understood that the shown embodiment of two restricted regions, two heating elements, four reagent compounds and four detectors is merely exemplary, and one, none, or any plurality of these elements can be mixed and matched as desired within a conduit depending upon the fluid to be tested and the tests to be performed.

A test commonly performed on a sample of blood is a titer test wherein blood is tested to see if it contains a specific type of antigen. A specific type of liter test is described in U.S. Pat. No. 5,318,897 to Paul, entitled MONOCLONIAL ANTIBODY AND ANTIBODY COMPONENTS ELICITED TO A POLYPEPTIDE ANTIGEN GROUND STATE. In such a titer test, whole blood is tested for a targeted antigen by mixing the blood with a reagent compound. The reagent compound includes magnetic particles joined to a labeled antibody and a capture antibody. When the blood sample and reagent compound are mixed, the targeted antigen, if present in the blood, bonds to the capture antibody in the reagent. Since the capture antigen is also coupled to a magnetic particle, the reaction thereby couples a magnetic particle to the targeted antigen. The antigens are then subjected to an electric field that biases the antigens against a conductive surface coated with a photoemitter. The impingement of the antigen with its magnetic particle against the photoemitter, causes the emittance of photons that can be optically detected. As such, if photons are detected, it is proved that the blood sample contained the targeted antigens. However, if no photons were detected, no target antigens are present.

In the prior art, devices designed to perform the above-identified titer test were highly complex. See for instance U.S. Pat. No. 5,093,268 to Leventis et al, entitled APPARATUS FOR CONDUCTING A PLURALITY OF SIMULTANEOUS MEASUREMENTS OF ELECTROCHEMILUMINESCENT PHENOMENA and U.S. Pat. No. 5,296,191 to Hall et al, entitled METHOD AND APPARATUS FOR CONDUCTING ELECTROCHEMILUMINESCENT MEASUREMENTS.

Figure 5:
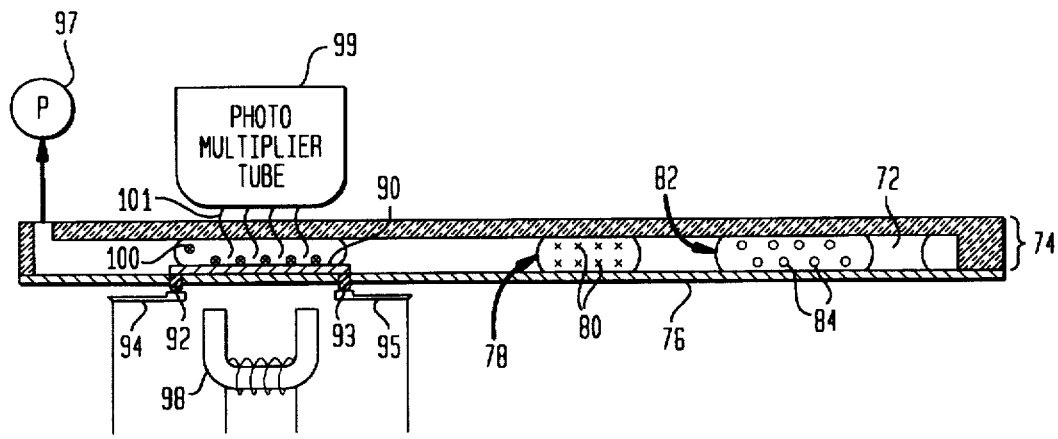
FIG. 5 is a cross-sectional view of an alternate embodiment of a cuvette, shown in conjunction with schematic representation of an alternate embodiment of a test apparatus.

Referring to FIG. 5, an embodiment of the present invention is adapted for use in performing a titer test such as that previously explained. The shown cuvette 70 can have one or any number of conduits 72 defined therein. The cuvette 72 has a transparent upper portion 74 into which the conduits 72 are formed. A substrate 76 is bonded to the upper portion defining the space of each conduit. The substrate 76 can be transparent but need not be. A conductive plate 90 is disposed on the substrate 76. The conductive plate 90 can be a strip of conductive material bonded to the substrate 76 or can be a thick or thin film conductor deposited upon the substrate 76. The conductive plate 90 is either a photoemissive material or is a conductive element coated with a photoemissive material for a purpose which will later be explained. Two electrical connectors 92, 93 extend through the substrate 76 and terminate at a point on the exterior of the cuvette 70.

As the cuvette 70 is inserted into a test machine, the electrical connectors 92, 93 abut against two electrical contacts 94, 95 that are used to supply a selected electrical bias to the conductive plate 90. As the cuvette 70 is properly inserted with a test machine, the conduit 72 couples to a pneumatic pump 97 and the conductive plate 90 aligns between an electromagnet 98 and a photo multiplier tube 99.

A reagent 78 is disposed within the conduit 72. The reagent contains molecules 80 that include a labelled antibody, a ferromagnetic micro particle and a capture antibody adapted to bond with a target antigen. A sample of whole blood 82 is drawn into the conduit 72 of the cuvette 70 in the same manner as was explained in the previous embodiments. The sample of blood 82 rehydrates the reagent 78, wherein the reagent 78 mixes with the antigens 84 present within the blood. The molecules 80 in the reagent 78 bond with the antigens 84 in the blood 82, thereby tagging each of the antigens 84 with a magnetic micro particle. The pneumatic pump 97 draws the sample of blood 82 onto the conductive plate 90 in between the electromagnet 98 and the photo multiplier tube 99. Once in position, the electromagnet 98 is enabled and the sample of blood 82 is exposed to the electromagnetic field. The electromagnetic field causes the antigen/micro particle 100 to migrate within the blood and impinge upon the conductive plate 90. As the antigen/micro particles 100 impinge upon the conductive plate 80, the photoemissive properties of the conductive plate coating or the conductive plate 90 itself causes photons 101 to be emitted when impinged upon by an antigen/micro particle 100. The photons 101 are detected and intensified by the photo multiplier tube 99 that creates a predetermined signal in response to the impinging photons. As a consequence, the production of photons by the photoemitter is indicative of the presence of a target antigen in the sample of blood. Furthermore, the intensity of the photons detected by the photo multiplier tube 99 is indicative of the concentration of target antigens contained within sample of blood.

Figure 6:
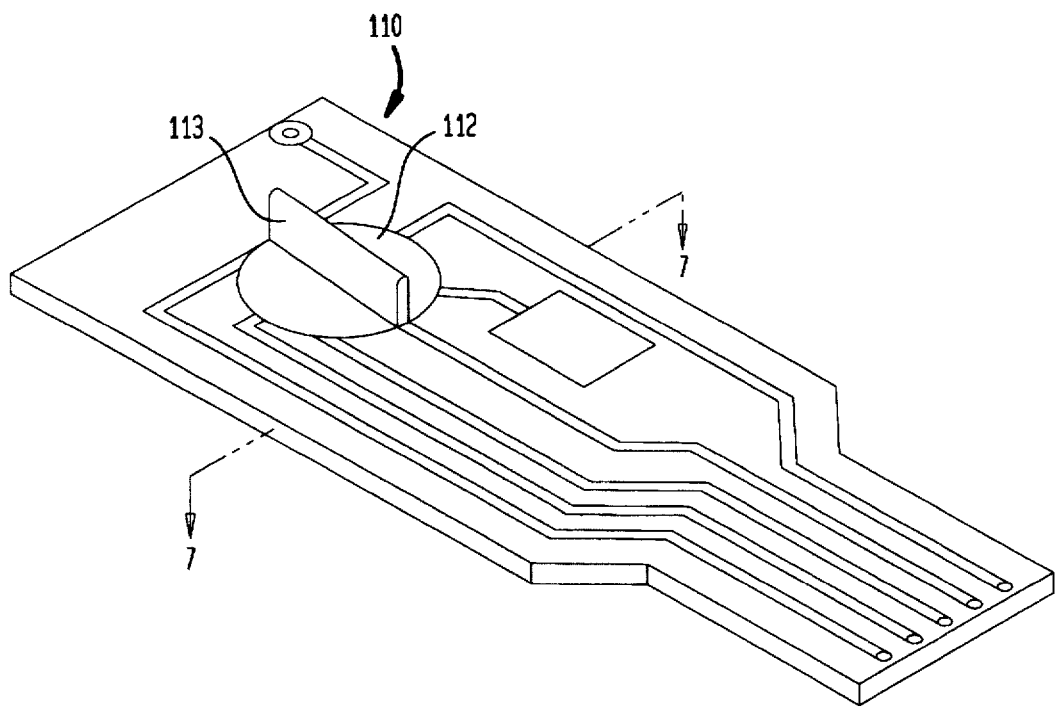
FIG. 6 is a perspective view of a second alternative embodiment of a cuvette.
Figure 7A:
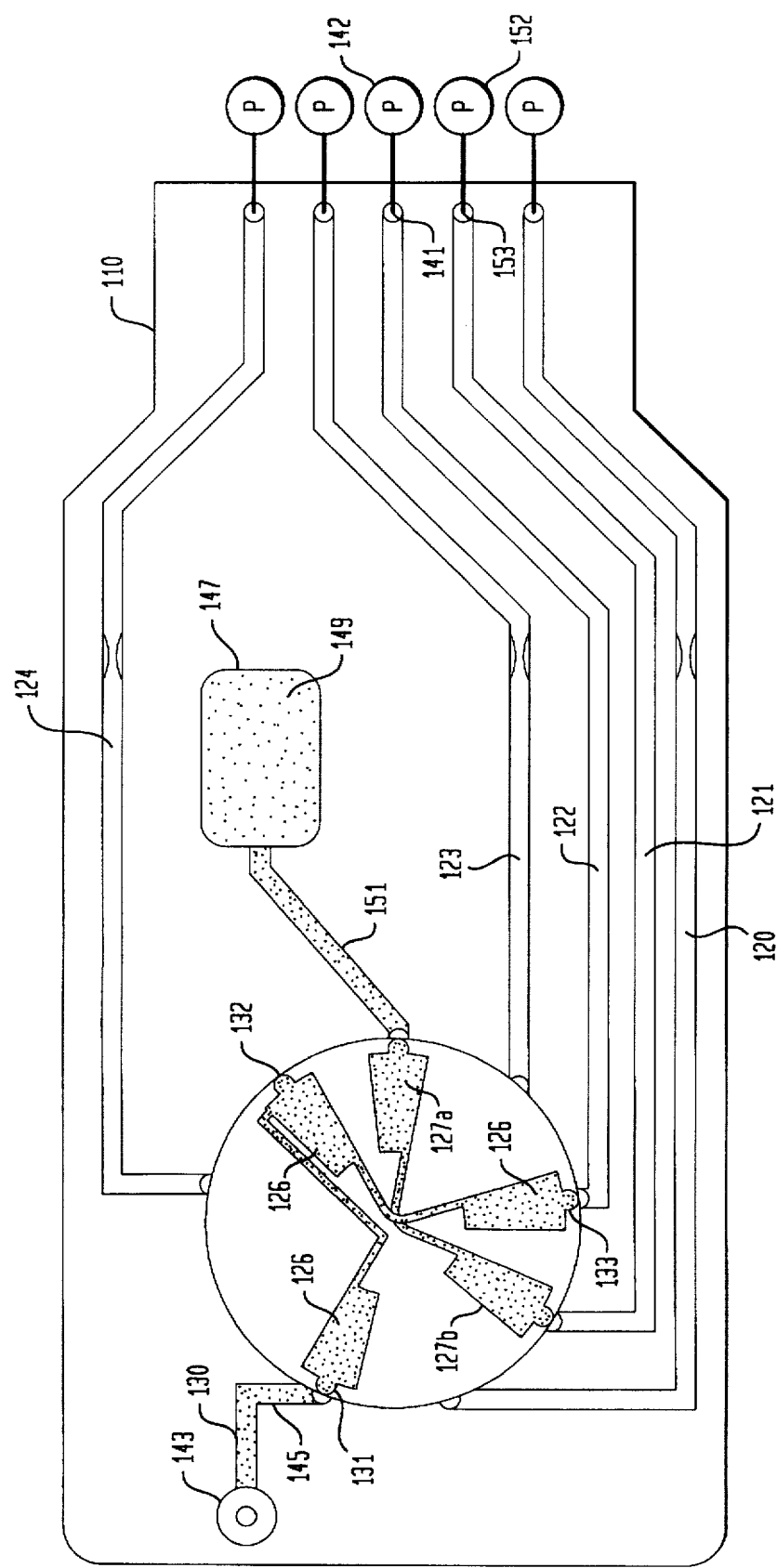

Referring to FIG. 6, an alternate embodiment of a cuvette 110 is shown having a manually manipulable valve manifold 112 contained therein. The valve manifold 112 has a knob 113 extending upwardly from its upper surface that enables the valve manifold 112 to be turned counter clock wise and/or clockwise about its center. In FIG. 7a, it can be seen that the various conduits 120, 121, 122, 123, 124, all converge at radial points surrounding the valve manifold 112. In the valve manifold 112 itself are two series of interconnected chambers. The two series of chambers include interconnected test sample chambers 126 and interconnected reagent chambers 127. As will be explained, either the test sample or the reagent is introduced into the various conduits by rotating the valve manifold 112 until the various chambers communicate with the conduits.

Figure 7C:
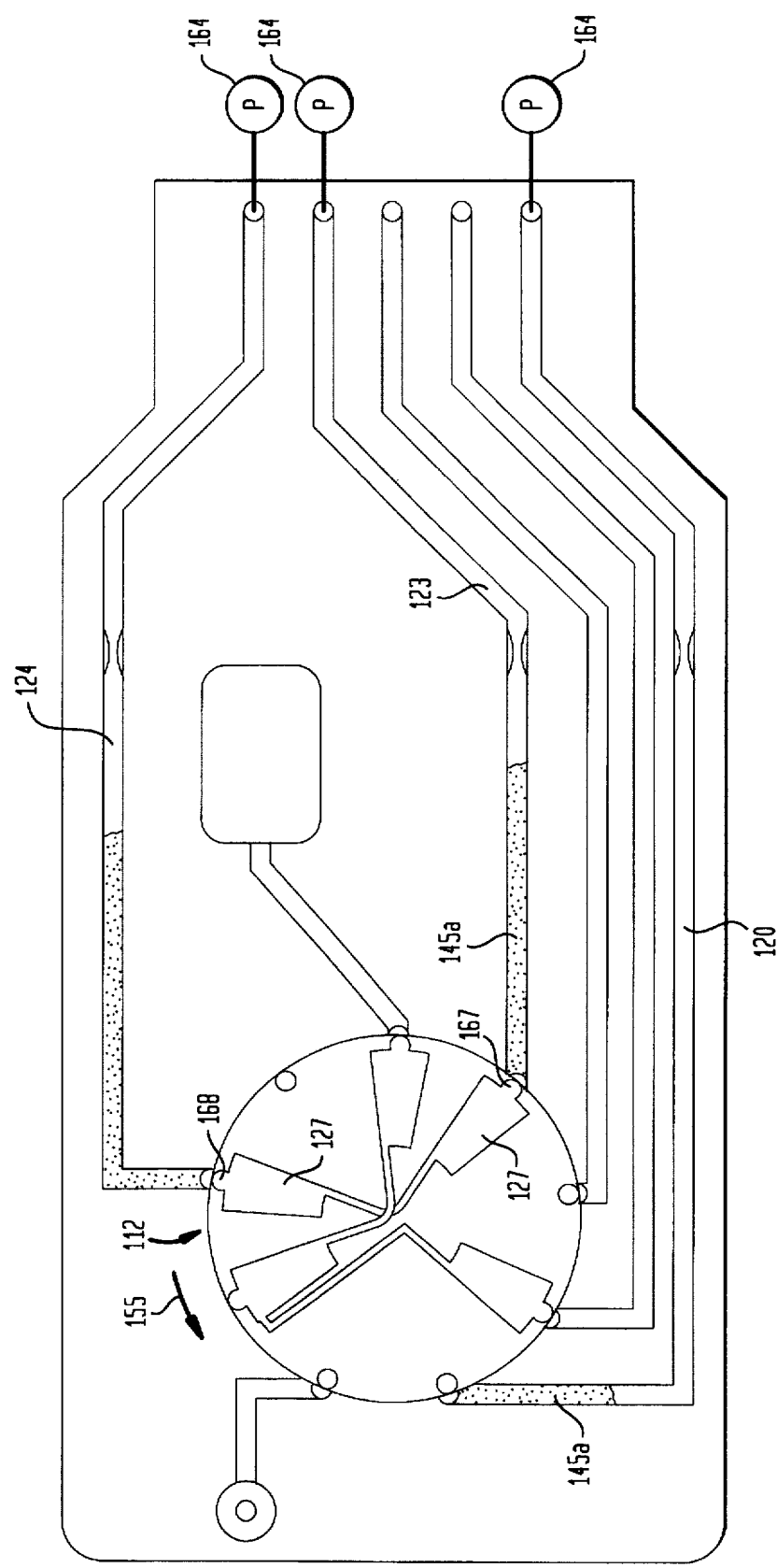

In the previous embodiments, the test sample was mixed with a dried reagent disposed within the cuvette. In the embodiment of FIGS. 6–7c, a configuration of the present invention is disclosed wherein a liquid reagent can be mixed with a test sample. In FIG. 7a, the valve manifold 112 is configured so that one of the test sample chambers 126 communicates with supply conduit 130 and another of the test sample chambers 126 communicated with fill pump conduit 122. In the shown embodiment, there are three test sample chambers that intersect three points 131, 132, 133 on the circumference of the valve manifold 112. In the shown orientation the first point 131 communicates with the supply conduit 130 and the third point 133 communicates with the first fill pump conduit 122. The first fill pump conduit 122 extends to the distal end of the cuvette 110, wherein the conduit terminates at a pumping port 141. When the cuvette is placed in a test machine, the pumping port 141 couples to a drawing pump 142 that creates a reduced pressure within the fill pump conduit 122. The supply conduit 130 terminates at a sample reservoir 143. The tester fills the sample reservoir 143 with a test fluid. As the drawing pump 142 reduces the pressure within the fill pump conduit 122, test fluid 145 is drawn out of the sample reservoir 143 and into the test sampler chambers 126 until those chambers are filled with the test fluid 145.

A reagent reservoir 147 is provided within the cuvette 110. The reagent reservoir 147 is filled with a liquid reagent 149 that is intended to be mixed with the test fluid 145. When the valve manifold 112 is in the position shown in FIG. 7a, the reagent reservoir 147 is coupled to a first of the reagent chambers 127a, via conduit 151. The distal reagent chamber 127b couples to a second fill pump conduit 121 that extends to pumping port 153. A pump 152 couples to the pumping port 153 creating a reduced pressure within the conduit 121. Although separate pumps may be used, it will be understood that a single pump may be used to reduce the pressure in both the first fill pump conduit 122 and the second fill pump conduit 121. The pump 152 draws reagent fluid 149 into the reagent chambers 127a and 127b until those chambers are full.

Referring to FIG. 7b, it can be seen that once the reagent chambers 127 are filled with reagent fluid 149 and the test sample chambers 126 are filled with test fluid 145, the valve manifold 112 is rotated in the direction of arrow 155 from the orientation of FIG. 7a to the orientation of FIG. 7b. Once in this orientation, the three salient points 131, 132, 133 of the test sample chambers 126 intersect three of the cuvette conduits 120, 123, 124. These three conduits 120, 123, 124 are the test conduits in which the test fluid 145 will be tested. Each of the test conduits 120, 123, 124 may contain a restricted region 160 or another obstacle to be used for mixing as has been previously explained. Furthermore, when the cuvette 110 is placed in a test machine the three test conduits 120, 123, 124 align under sensors capable of detecting some physical and/or chemical attribute of the test fluid 145 contained within the test conduits 120, 123, 124.

As is seen in FIG. 7b, the three test conduits 120, 123, 124 lead to pumping ports 161, 162, 163 that join those conduits to a pneumatic source 164. The pneumatic source can be three individual pumps or one single pump. The pumps 164 are any pumps capable of selectively increasing and decreasing the pressure within the test conduits 120, 123, 124. In FIG. 7b, the pumps 164 are used to draw a sample 145a of the test fluid into each of three test conduits 120, 123, 124. Once a predetermined amount of fluid is drawn into each of the test conduits 120, 123, 124, the pumps stop and hold each of the samples 145a in a steady position.

Referring to FIG. 7c, the valve manifold 112 has been rotated again in the direction of arrow 155, from the orientation of FIG. 7b to the orientation of FIG. 7c. In this orientation, the salient points 167, 168 of the two reagent chambers 127 align with two of the conduits 123, 124. The pumps 164 are then used to draw the reagent fluid 149 into two of the test conduits 123, 125, immediately adjacent to the sample fluid 145a. The sample 145a contained in the first test conduit 120 does not become mixed with a reagent fluid 149. As a result, the sample 145a in the first test conduit 120 can be used as a control sample to quantify the samples in the other two conduits.

Referring to FIG. 7d, the valve manifold 112 has been rotated yet again in the direction of arrow 155, from the orientation of FIG. 7c to the shown configuration of FIG. 7d. In this orientation, vent holes 170 align with the three test conduits 120, 123, 124. The pumps 164 can then draw the fluids further into the conduits for testing. The reagent fluid 149 in the two test conduits 123, 124 is mixed with the sample fluid 145a. The two fluids are mixed by being moved back and forth across the restricted region 160. The mixture is then tested in the manner previously described in regard to earlier embodiments.

In the shown embodiment, two conduits 123, 124 are used to test the reagent/test sample mixture and one conduit 120 is used to test the test sample alone. Such a configuration is merely exemplary and it should be understood that any number of conduits could be used to test the fluids, wherein the concentrations of fluids in each conduit need not be the same. As a result, different tests can be conducted in the different conduits.

Figure 8:
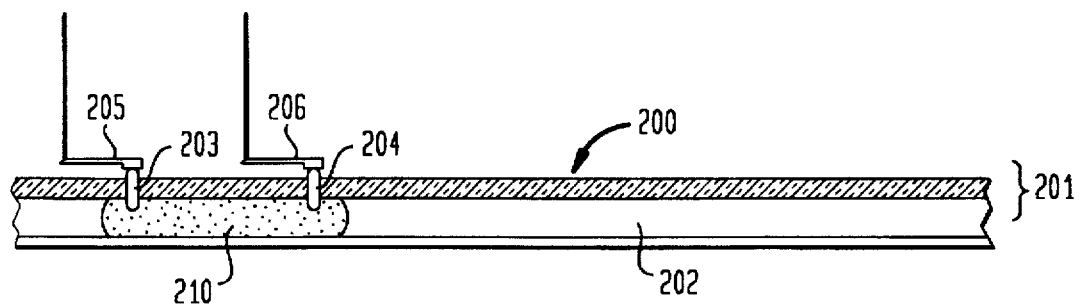
FIG. 8 is a segmented cross-sectional view of a third alternative embodiment of a cuvette.

Referring to FIG. 8, a segment of a cuvette 200 is shown wherein conductive leads 203, 204 extend through the upper portion 201 of the cuvette 200 and lead into a conduit 202 defined by the cuvette 200. As the cuvette is placed within a testing machine, the conductive leads 203, 204 engage contacts 205, 206, thereby electrically coupling the conductive leads 203, 204 to the testing machine. When a test sample 210 is drawn into the conduit 202 and into a position where the test sample 210 contacts both conductive leads 203, 204 then the sample 210 can be electrically tested. For example, by providing opposite electrical biases to the two conductive leads 203, 204, current can be caused to flow through the test sample. This provides an electrical impedance valve for the test sample 210 that might be indicative of an ion concentration in the sample or another physical/chemical characteristic.

Figure 9:
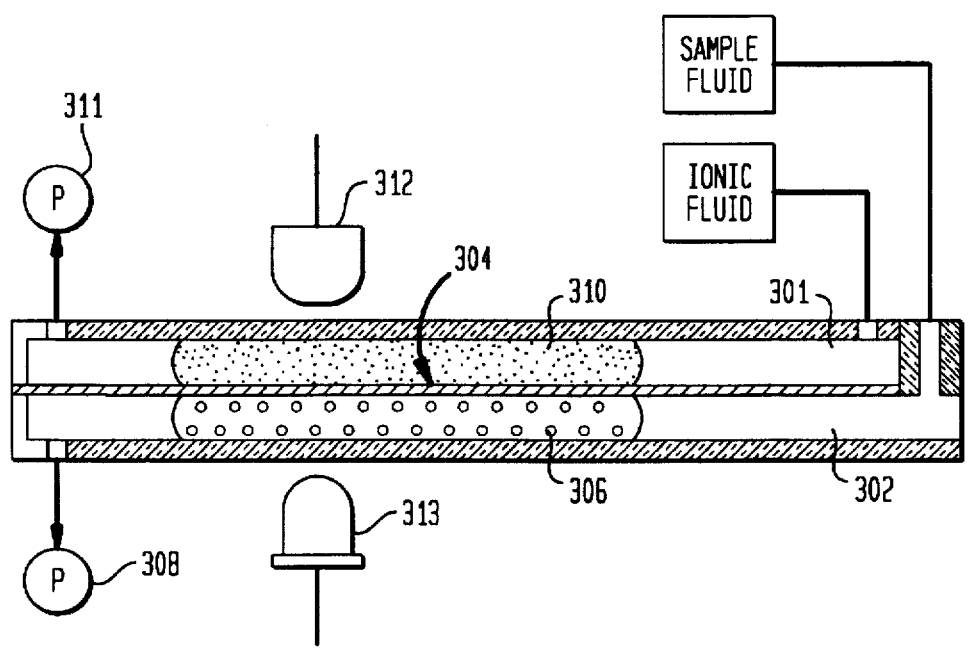
FIG. 9 is a cross-sectional view of a fourth alternative embodiment of a cuvette shown in conjunction with a schematic representation of a test apparatus and containing both sample fluid and ionic fluid.

Referring to FIG. 9, another embodiment of the present invention is shown where the cuvette 300 contains conduits 301, 302 separated by a filtering membrane 304. In the shown embodiment, sample fluid 306 is drawn into the lower conduit 301 by the first pump 308. Ionic fluid 310 is drawn into the upper conduit 302 by the second pump 311. Osmotic pressure causes the sample fluid 306 to selectively pass through the filtering membrane 304 and leach into the ionic fluid 310. The second pump 311 then moves the sample fluid 300 away from the area of the photodetector 312. Light from a light source 313 is shown through the ionic fluid 310, whereby the nephelometry of the ionic fluid 310 can be measured. The measured nephelometry provides an indication as to the composition of the sample fluid 306 depending upon which type of filtering membrane is used.

This disclosure provides multiple cuvette configurations and multiple ways to measure a test fluid contained within a cuvette. The shown embodiments are merely exemplary and it should be understood that the various configurations shown in the different embodiments can be mixed and matched as desired into configurations that are not specifically shown. Also a person skilled in the art may make variations and modifications to the described embodiments utilizing functionally equivalent components to those described. All such equivalent components, variations and modifications are intended to be included within the scope of this invention as defined by the appended claims.

What is claimed is:

1. A device for testing a fluid sample, comprising:
   a cuvette that defines at least one conduit therein, said at least one conduit having a first end and a second end, wherein said first end has an inlet port opening to a surface of said cuvette for receiving said test fluid;
   at least one reagent compound disposed within said at least one conduit between said first end and said second end;

means for introducing a predetermined volume of said fluid sample into each said conduit through said inlet port;

pumping means for selectively moving said predetermined volume of said fluid sample from a first position in said conduit to a second position;

mixing means disposed in said conduit disposed between a first position and a second position for physically mixing said fluid sample in said conduit with said at least one reagent, said mixing means taking effect when said pumping means moves said fluid sample from said first position, past said mixing means, to said second position in said conduit; and testing means for testing a characteristic associated with said predetermined volume of fluid sample.

2. The device according to claim 1, wherein said at least one reagent compound is dried and said fluid sample rehydrates said at least one reagent compound within said conduit as said fluid sample moves from said first position to said second position.

3. The device according to claim 1, wherein said cuvette defines a plurality of conduits, wherein said at least one reagent compound is disposed in at least one of said conduits.

4. The device according to claim 1, wherein said pumping means is contained in a machine that pneumatically couples to said inlet port disposed at said first end of said cuvette when said cuvette is selectively inserted into the machine.

5. The device according to claim 1, wherein said testing means includes a source of electromagnetic radiation disposed along said at least one conduit between said first and second ends, and a detector for detecting electromagnetic radiation oppositely disposed to said source of electromagnetic radiation, such that said at least one conduit is positioned between said source of electromagnetic radiation and said detector of electromagnetic radiation, wherein said source provides electromagnetic radiation that passes through said cuvette prior to being detected.

6. The device according to claim 1, wherein said testing means includes a means for inducing photoluminescence with said fluid sample and a detector for detecting the photoluminescence.

7. The device according to claim 1, further including at least one heating element disposed proximate a predetermined portion of said conduit, whereby the temperature of said sample can be selectively raised within said predetermined portion of said conduit.

8. The device according to claim 1, further including a plurality of heating elements disposed proximate said conduit, whereby the temperature of said fluid sample can be controlled in separate sections of said conduit.

9. The device according to claim 1, further including a filtering means disposed in said conduit for selectively filtering selected components associated with said fluid sample.

10. The device according to claim 3, further including a filtering means disposed in each of a plurality of said conduits, wherein said filtering means filter separate components associated with said fluid sample.

11. The device according to claim 1, further including a pressure sensor for measuring pneumatic pressure in said conduit.

12. The device according to claim 1, wherein said mixing means includes at least one projection that protrudes into said conduit that causes turbulence in said fluid sample as said fluid sample flows between said first position and said second position.

13. The device according to claim 1, wherein said mixing means includes at least one restricted region disposed between said first position and said second position.

14. A device for testing blood, comprising:

a cuvette that defines at least one conduit therein, said at least one conduit having a first end and a second end, wherein said first end has an inlet port opening to a surface of said cuvette for receiving said test fluid;

at least one reagent compound disposed within said at least one conduit between said first end and said second end;

means for introducing a predetermined volume of said fluid sample into each said conduit through said inlet port;

pumping means for selectively moving said predetermined volume of said fluid sample from a first position in said conduit to a second position;

mixing means disposed in said conduit disposed between a first position and a second position for physically mixing said fluid sample in said conduit with said at least one reagent;

testing means for testing a characteristic associated with said predetermined volume of fluid sample, wherein said at least one reagent compound includes magnetic particles and capture antibodies attached to said magnetic particles, whereby said magnetic particles and capture antibodies bond to target antigens if present in the blood.

15. The device according to claim 14, further including a means for creating an electromagnetic field, whereby a target antigen bound to the magnetic particles can be selectively manipulated to a predetermined position by the electromagnetic field.

16. The device according to claim 15, further including a photoemitter disposed with said cuvette for emitting photon when impinged upon by the target antigen.

17. The device according to claim 14, further including conductive probes that extend from an internal point within said cuvette to an external point on the exterior of said cuvette, said conductive probes capable of contacting said fluid sample in said cuvette when said fluid sample is disposed in a predetermined position.

18. The device according to claim 17, wherein said testing means includes a means for passing current through said fluid sample to ascertain the impedance associated with the fluid sample.

19. A cuvette for use in testing a fluid sample, said cuvette comprising:

a plurality of conduits within said cuvette, each of said conduits terminating at a first end at separate pumping ports and terminating at a second end at a common supply port, wherein said conduits are of a predetermined size that is sufficiently wide such that capillary action is avoided and whereby the fluid sample is introduced into each of said conduits via said supply port;

at least one reagent disposed in at least one of said conduits, wherein said at least one reagent mixes with the fluid sample when brought in contact therewith and;

at least one mixing obstruction disposed in at least one of said conduits, wherein said mixing obstruction creates turbulence in the fluid sample when the fluid sample flows therepast such that the fluid mixes within said conduit.

20. The cuvette according to claim 19, wherein said cuvette is substantially transparent, wherein said at least one reagent comprises a dried compound that is rehydrated by the fluid sample when brought in contact therewith, and wherein the effect of said reagent on the fluid sample serves as an indicator whether the fluid sample contains a targeted substance.

21. The cuvette according to claim 19, wherein said cuvette includes a solid upper region having a first surface into which are formed a plurality of grooves and a lower region made of a thin laminate having at least one layer that is bonded to said first surface, wherein said thin laminate and said grooves combine to define said plurality of conduits.

22. The cuvette according to claim 19, further including electrical connections that extend from a first point within said cuvette to a second point external of said cuvette.

23. The cuvette according to claim 19, further including a photoemitter, disposed within at least one of said conduits.

24. The cuvette according to claim 19, further including a filtering means disposed within at least one of said conduits, for selectively filtering separate components associated with the fluid sample.

25. A device for detecting the presence of an analyte in a blood sample, said device comprising:
   a) a cuvette that includes:
      i) at least one conduit that extends from a supply port to a pumping port for receiving the blood sample, wherein a certain air pressure is created within the conduit;
      ii) a reagent disposed within said conduit having a magnetic particle coupled to an antibody, wherein said antibody will bind to the analyte when mixed with the blood sample if the analyte is present in the blood sample;
      iii) a photoemitter means for emitting photons when impinged upon by the magnetic particle;
   b) a testing machine having at least one pump for increasing or decreasing the pressure in said at least one conduit, wherein said at least one pump on said testing machine is aligned to couple to at least one conduit of said cuvette; wherein said testing machine further comprises:
      i) means for selectively exposing the blood sample in said cuvette to an electromagnetic field, wherein said electromagnetic field causes the magnetic particles to impinge upon said photoemitter means;
      ii) a photodetector for detecting photons emitted by said photoemitter.

26. A cuvette for use in testing a fluid sample, said cuvette comprising:
   a manifold assembly having a plurality of ports thereon said ports being radially aligned relative to the center of the manifold assembly, wherein the orientation associated with said plurality of ports will change when said manifold assembly is rotated in a clockwise or counterclockwise position; and
   a plurality of conduits leading to said manifold assembly wherein said manifold assembly selectively couples selected sets of said conduits to said plurality of ports depending upon how said manifold assembly is rotated.

27. The cuvette according to claim 26, further including at least one reservoir, wherein at least one of said conduits extends from said at least one reservoir to said manifold assembly.

28. The cuvette according to claim 26, wherein said manifold assembly includes at least one reservoir therein, whereby a sample can be obtained from one of said conduits and transferred to another of said conduits as the rotary position of said manifold assembly is changed.

29. The cuvette according to claim 26, further including a supply port through which the fluid sample can be introduced into at least one of said conduits that lead to said manifold assembly.

30. A method of testing a fluid sample for the presence of a targeted substance, comprising the steps of:
   providing a cuvette having at least one conduit therein, wherein said at least one conduit has a reagent disposed therein, said reagent having a predetermined characteristic relative to the targeted substance;
   introducing the fluid sample into the cuvette;
   pneumatically pumping the fluid sample within said at least one conduit between a first position and a second position, whereby the fluid sample is caused to mix with said reagent;
   measuring a characteristic associated with the fluid sample to determine the effect of said reagent on the fluid sample, wherein said effect serves as an indicator whether the fluid sample contains the targeted substance.

31. The method according to claim 30, further including providing an obstruction in said at least one conduit, wherein said obstruction causes turbulence in the fluid sample as the sample is pumped between said first position and said second position.

32. The method according to claim 30, further including selectively heating the fluid sample at least one point between said first position and said second position.

33. The method according to claim 31, further including providing multiple reagents at separate points in said at least one conduit wherein the fluid sample is moved past at least one said obstruction each time the sample mixes with one of said multiple reagents.

34. The method according to claim 30, further including the step of providing a filtering element in said at least one conduit, wherein said filtering element selectively filters out components of the flow sample thereby preventing those components from advancing past said filtering element.

35. The method according to claim 30, wherein said cuvette has multiple conduits that leads to a common supply port, wherein different reagent combinations are disposed in the separate conduits whereby different tests can be performed on the same sample in the same conduit.

* * * * *